United States Patent
Solomon et al.

(10) Patent No.: US 8,158,148 B2
(45) Date of Patent: *Apr. 17, 2012

(54) PHARMACEUTICAL TABLETS COMPRISING TWO OR MORE UNITARY SEGMENTS

(75) Inventors: Lawrence Solomon, Boca Raton, FL (US); Allan S. Kaplan, Boca Raton, FL (US)

(73) Assignee: Accu-Break Technologies, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/598,315

(22) PCT Filed: May 23, 2005

(86) PCT No.: PCT/US2005/018631
§ 371 (c)(1),
(2), (4) Date: Apr. 8, 2008

(87) PCT Pub. No.: WO2005/112900
PCT Pub. Date: Dec. 1, 2005

(65) Prior Publication Data
US 2008/0233189 A1    Sep. 25, 2008

(51) Int. Cl.
*A61K 9/44* (2006.01)
*A61K 9/20* (2006.01)
*A61K 31/353* (2006.01)
*A61K 31/585* (2006.01)
*A61K 31/197* (2006.01)

(52) U.S. Cl. ........ 424/467; 424/464; 514/457; 514/175; 514/567

(58) Field of Classification Search ................... 424/467, 424/464; 514/457, 175, 567
See application file for complete search history.

(56) References Cited

U.S. PATENT DOCUMENTS

| | | | |
|---|---|---|---|
| 3,128,226 A | | 4/1964 | Rubin, at al. |
| D201,497 S | | 6/1965 | Ninger |
| 3,696,091 A | * | 10/1972 | Eberlin et al. ............. 536/5 |
| 3,723,614 A | * | 3/1973 | Langauer ................. 424/467 |
| 3,927,194 A | | 12/1975 | Geller |
| 4,215,104 A | | 7/1980 | Ullman et al. |
| 4,786,507 A | * | 11/1988 | Schmidt .................. 424/472 |
| 4,824,677 A | * | 4/1989 | Shah et al. ............... 424/467 |
| 5,041,430 A | * | 8/1991 | Addicks et al. ........... 514/161 |
| 5,817,340 A | | 10/1998 | Roche et al. |
| 6,086,919 A | | 7/2000 | Bauer et al. |
| 6,183,778 B1 | * | 2/2001 | Conte et al. ............... 424/472 |
| 6,294,200 B1 | | 9/2001 | Conte et al. |
| 6,309,668 B1 | | 10/2001 | Bastin et al. |

(Continued)

FOREIGN PATENT DOCUMENTS
CH   648754   4/1985
(Continued)

OTHER PUBLICATIONS
Lieberman, Herbert et al., Pharmaceutical Dosage Forms-tablets, 1980, Informa Health Care, vol. 1, pp. 132 and 274.

(Continued)

*Primary Examiner* — Robert A Wax
*Assistant Examiner* — Aradhana Sasan
(74) *Attorney, Agent, or Firm* — Ted W. Whitlock; James V. Costigan

(57) ABSTRACT

Accurate means of dosing with a compressed, segmented pharmaceutical tablet, and tablettes formed from said tablets, is disclosed.

18 Claims, 7 Drawing Sheets

U.S. PATENT DOCUMENTS

| | | | |
|---|---|---|---|
| 6,555,581 B1 * | 4/2003 | Franz et al. | 514/567 |
| 6,919,373 B1 | 7/2005 | Lam et al. | |
| 7,011,849 B2 | 3/2006 | Storm et al. | |
| 7,318,935 B2 * | 1/2008 | Solomon et al. | 424/464 |
| 7,329,418 B2 * | 2/2008 | Solomon et al. | 424/464 |
| 2002/0132850 A1 | 9/2002 | Bartholomaeus | |
| 2004/0167207 A1 * | 8/2004 | Nesselroad, III | 514/457 |
| 2005/0038039 A1 | 2/2005 | Fanara et al. | |
| 2006/0280794 A1 | 12/2006 | Hamaguchi et al. | |
| 2007/0031494 A1 * | 2/2007 | Solomon et al. | 424/472 |

FOREIGN PATENT DOCUMENTS

| | | | |
|---|---|---|---|
| WO | WO 00/18447 | * | 4/2000 |

OTHER PUBLICATIONS

H.A. Lieberman and L. Lachman, Pharmaceutical Dosage Forms, vol. 1, pp. 217-223, Marcel Dekker, Inc., New York, New York, 1989.

* cited by examiner

PHARMACEUTICAL TABLETS COMPRISING TWO OR MORE UNITARY SEGMENTS

FIELD OF THE INVENTION

The invention is concerned with a pharmaceutical tablet containing at least three segments, two of which are compositionally identical and are formed from the same layer or layers. The invention addresses imprecise breaking of pharmaceutical tablets.

BACKGROUND OF THE INVENTION

Pharmaceutical tablets have long been produced with an indentation known as a score, which both locates and tends to physically assist in breaking said tablets into smaller units, called tablettes herein, that are intended to serve as dosage forms. Unfortunately, numerous problems have attended breaking scored tablets, as delineated:

Many drugs require dosage adjustments, such as warfarin, the scored tablets of which are frequently broken. These dosage adjustments through tablet breaking by patients have been determined to be imprecise. As the following discussion demonstrates, for many years experts have called upon the pharmaceutical industry to improve the quality of tablet breaking, yet such has not been optimized until the current invention.

In 1984, Stimpel et al, ("Stimpel"), described the relative accuracy of breaking of various tablets for treatment of cardiovascular problems. M. Stimpel et al., "Breaking Tablets in Half." *The Lancet* (1984):1299. Even though breaking was performed by a sophisticated, dexterous person, Stimpel found that breaking was not accurate, and opined that real world use by patients would provide yet more unsatisfactory results. Stimpel called upon the pharmaceutical industry to improve the accuracy of splitting tablets: "Clearly any assumption that halving a tablet will not lead to inaccurate doses is invalid. This potential source of inaccuracy could be even more significant in clinical situations (our study was done under ideal conditions) and the pharmaceutical industry should tackle it, either by improving divisibility (as already has been done for lopressor and logroton) or, even better, by marketing a wider range of unscored tablets to provide all the doses that might be indicated clinically."

Despite that finding and statement, and despite the issuance of various patents relating to optimizing a scoring pattern and/or tablet shape, Rodenhuis et al., (2004) noted that: "Improving the functioning of score lines may be a more practical approach than banning this dosage form." (emphasis added). N. Rodenhuis et al., "The rationale of scored tablets as dosage form." *European J. of Pharmaceutical Sciences* 21 (2004):305-308 (hereafter "Rodenhuis"). Rodenhuis observed that European regulatory authorities started a policy to discourage scoring of tablets in 1998. This policy change, according to Rodenhuis, likely related to "many recent reports of bad functioning score lines", that "many scored tablets are difficult to break", and that "many scored tablets show unsatisfactory mass uniformity of the subdivided halves". The authors then go on to describe useful aspects of scoring tablets. For a comprehensive review article on this topic, see van Santen, E., Barends, D. M. and Frijlink, H. W. "Breaking of scored tablets: a review." *European J. of Pharmaceutics and Biopharmaceutics* 53 (2002):139-145.

Some current studies that demonstrate the severity of the problem are described below.

Peek et al., (2002), studied tablet splitting by "elderly patients" aged 50-79. Peek, B. T., Al-Achi, A., Coombs, S. J. "Accuracy of Tablet Splitting by Elderly Patients." *The Journal of the American Medical Association* 288 No. 4 (2002): 139-145. Breaking scored tablets with mechanical tablet splitters without specific instruction led to highly unsatisfactory separating of the tablets. For example, warfarin 5 mg was on average split into 1.9 and 3.1 mg tablets. This potent anticoagulant has such a narrow therapeutic range that 2, 2.5, and 3 mg tablet doses are manufactured. Biron at al., (1999), demonstrated that warfarin 10 mg also often split to less than 4.25 or greater than 5.75 mg. Giron, C., Liczner, P., Hansel, S., Schved, J. F., "Oral Anticoagulant Drugs: Do Not Cut Tablets in Quarters." *Thromb Haemost* 1201 (1999). In addition, they demonstrated that loss of mass due to crumbling or chipping due to breaking of the warfarin tablets was statistically significant. They also demonstrated that quartering of the tablets was grossly inaccurate.

McDevitt et al., (1998), found that 25 mg unscored hydrochlorothiazide (HCTZ) tablets were manually split badly enough that 12.4% deviated by more than 20% from ideal weight. McDevitt, J. T., Gurst, A. M., Chen, Y. "Accuracy of Tablet Splitting." *Pharmacotherapy* 18. No. 1 (1998):193-197. 77% of the test subjects stated that they would be willing to pay a premium for individually produced 12.5 mg HCTZ tablets rather than split unscored 25 mg tablets.

Rosenberg et al., (2002), studied pharmacist-dispensed split tablets. Rosenberg, J. M., Nathan, J. P., Plakogiannis, F. "Weight Variability of Pharmacist-Dispensed Split Tablets." *Journal of American Pharmaceutical Association* 42 No. 2 (2002):200-205. They found that "tablet splitting resulted in an unacceptably high incidence of weight variation." They recommended that "standards should be developed to ensure uniformity of split tablets."

Teng et al., (2002), using a trained individual in a laboratory setting to split tablets, concluded that "the majority of the 11 drug products we tested, when assessed for their ability to be split into half-tablets of equal dose, failed a liberally interpreted USP (United States Pharmacopeia) uniformity test.... The practice of dividing tablets to save costs or to improve a dosage regimen ... is not recommended for patients using drugs with more substantial toxicity and steep dose-response efficacy curves." Teng, J., Song, C. K., Williams, R. L., Polli, J. E. "Lack of Medication Dose Uniformity in Commonly Split Tablets." *Journal of American Pharmaceutical Association* 42 No. 2 (2002):195-199.

Rodenhuis reported that 31 of all tablets in one Netherlands study were subdivided before being swallowed. In the U.S., many "managed care" insurance organizations encourage patients to split tablets which may be unscored and irregularly-shaped. Many drug products in the US are either unscored or are provided as capsules despite being able to be produced as tablets.

In the spirit of improving the above problems, the inventors have devised improvements in tablet design and structure as demonstrated below.

SUMMARY OF THE INVENTION

The invention provides novel pharmaceutical tablets having compositionally substantially identical first and second "unitary segments" that each adjoin the same face (surface) of a compositionally distinct first non-unitary segment. Said pharmaceutical tablets preferably comprise two or more compositionally identical unitary segments including a first unitary segment and a second unitary segment, said first unitary segment and said second unitary segment containing a drug or drugs, said first and second unitary segment having been formed from the same layer or layers that was or were divided; said first segment optionally having a score on its surface positioned between said first and said second unitary segments; said tablet optionally having additional unitary segments; and said tablet having at least one segment that is not a unitary segment.

The pharmaceutical tablet as defined herein may have one or more additional unitary segments in addition to said first and second unitary segments that are optionally present and that are derived from the same layer or layers as said first and second unitary segments.

The invention involves pharmaceutical tablets that are most conveniently produced as compressed tablets.

A preferred machine with which to produce said tablets is a bi-layer, tri-layer, or five-layer tablet press (or, tabletting machine).

As described herein, the preferred method of making the tablet of the invention utilizes a protuberance known as an embossing that rises from the lower punch of a tablet die in a tabletting machine. In a preferred method of manufacturing, a granulation preferably containing a therapeutic amount of an active pharmaceutical ingredient enters the die, preferably forms a layer above the highest point of said embossing, and is tamped by the upper punch. Next, a second granulation that is different from said first granulation enters said die on top of said first granulation, preferably is tamped by the upper punch, and then the tablet is compressed by the upper punch so that said compression pushes said first granulation below the highest points of said embossing. In the invention, said embossing occupies a position on the lower punch that may bisect or quadrisect said lower punch, so that said compression causes said first layer to be divided into two or more non-contiguous segments. Said first layer formed from said first granulation is herein referred to as a divided layer; said segments formed from a divided layer are herein referred to as unitary segments. The invention therefore allows precise division of said tablet, when desired, by allowing breaking to occur only through the second layer that was formed by said second granulation so that maximal accuracy of dosing with a tablet fragment arising from intentional tablet breaking may occur. In the above example, said second granulation preferably lacks an active drug (i.e., it is an inactive granulation).

Less preferred methods than the above of manufacturing tablets of the invention are disclosed subsequently.

When tablets of the invention are broken, the term "tablette" is utilized herein to denote the major fragments arising from said breaking. Breaking a tablet as in FIG. 1 through a bisecting score creates two tablettes, each containing very similar quantities of active ingredients if the tablet is broken through a largely inactive segment. Small chips and crumbs that typically are formed when a tablet is broken are not considered tablettes.

The invention preferably utilizes the term "segments" in describing the structure of a tablet. The discrete, non-contiguous parts of a divided layer are considered to be segments. Less preferred but possible is a situation in which two substantially identical layers enter the die first and second, are followed by a third, different layer, and then compression pushes both of the first two granulations (which are the first two layers) below the highest point of the embossing arising from the lower punch, forming unitary segments. In this case, it is not one but two layers that are part of the structure of each unitary segment.

The invention also utilizes the above-described structure as a core structure that is part of a tablet with segments arising from undivided layers and/or additional unitary segments.

Accordingly, it is a primary object of the invention to provide a novel tablet that is adapted to be broken into two or more substantially predeterminable doses of a drug or drugs by creating tablettes each containing fewer unitary segments than are present in the whole tablet.

It is also an object of the invention to provide a novel tablet that if crumbs or chips are formed by said tablet breaking, the quantity of active drug that is lost is minimized.

It is also an object to provide novel tablets adapted to contain drugs with a narrow therapeutic index or that otherwise have significantly different therapeutic or toxic effects with relatively modest alterations in dosage, such as warfarin sodium and L-thyroxine.

Because of the fine tolerances of less than one (1) mm involved in the process of manufacturing the tablets of the invention, every tablet may not include unitary segments. However, it is also within the scope of the invention to produce tablets lacking unitary segments, but having a score which penetrates so deeply within a first segment containing a drug towards a second segment that a pharmaceutical tablet with a first segment containing a drug or drugs in which a score that penetrates 95-99% or more of the distance between the origin of said score and the interface between said first and second segments is a part of the present invention. Stated another way, if less than 5% of the mass of a first segment lies between the length of a score that traverses said first segment and the interface between said first and a second segment, then said tablet is also within the scope of the present invention.

These and other objects of the invention will become apparent from the present specification.

DETAILED DESCRIPTION OF THE INVENTION

Figure 1:
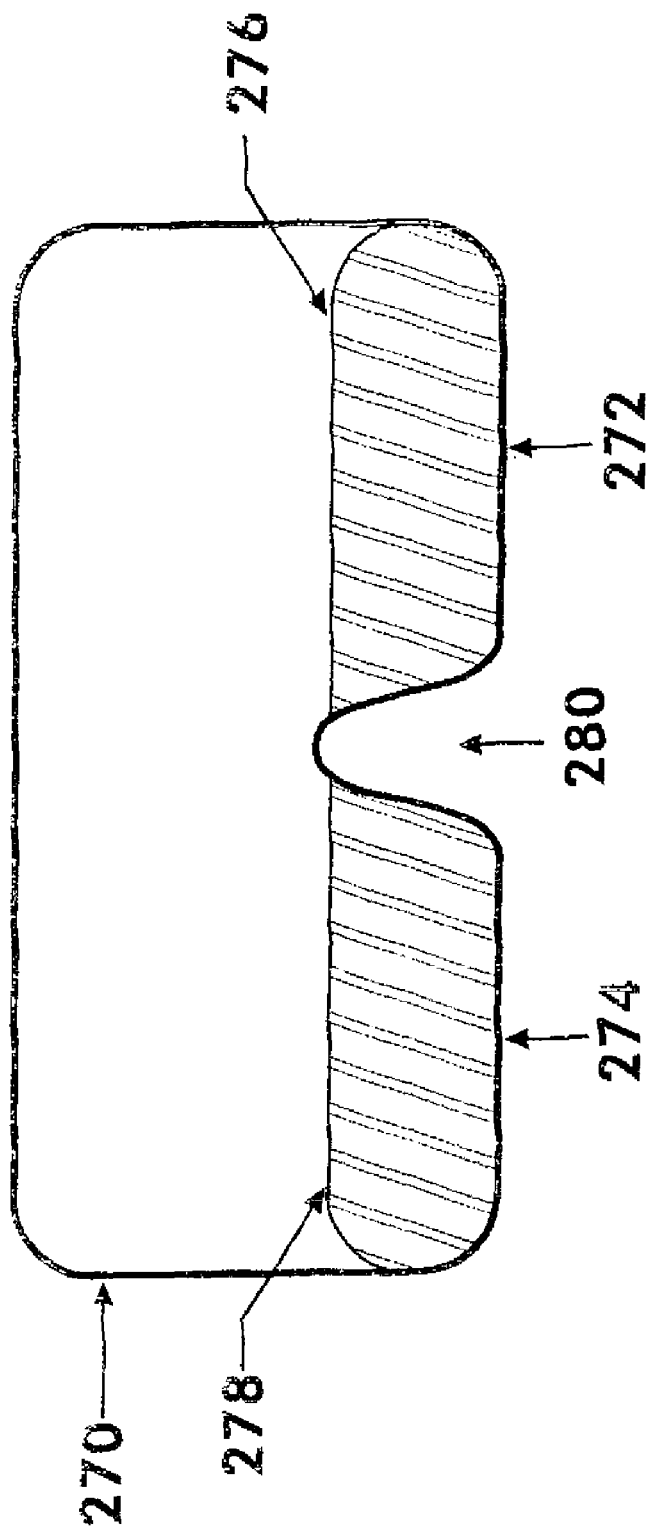
FIG. 1 depicts a cross-section of a three-segment tablet with one score.

Before describing the present invention in detail, it is to be understood that this invention is directed to pharmaceutical tablets, preferably those pharmaceutical tablets which are made by compression such as by compression applied in a die in an automated tabletting machine, and preferably those pharmaceutical tablets that are uncoated. Tablets of the invention are not formed using a cement, glue, adhesive, or the like.

If desired, conventional film coatings may be applied to enhance the appearance of the tablets and to facilitate the handling of the tablets. It is also to be understood that in describing and claiming the present invention, the following definitions have been utilized:

A segment represents the entirety of a contiguous, substantially homogeneous part of a tablet or tablette (see below) of the invention.

A compressed layer that is not adjacent to a layer formed from a substantially identical granulation that formed said first-mentioned layer is a "simple segment." Tablets of the invention comprise two or more segments, and each segment may be formed from two or more layers.

The term "unitary segment" means a physically separated, non-contiguous part of a divided layer or layers of a tablet and which may be made using a bottom embossed die that causes granulate to be divided as it enters the tablet die or after compression by an upper punch in the die; or, by a post-tabletting scoring that removes a part of a segment to a depth that exposes an underlying segment.

A layer is produced by introducing an amount of an individual granulation into a tablet die to fill at least a part of the die. A layer is considered to exist whether it is in the form of an un-tamped, tamped or fully compressed granulation. Because some migration of granulation may take place in the tabletting machine, some amount (preferably of no therapeutic importance) of a granulation that forms one layer may be transferred to another layer.

The terms "active agent," "drug," "active drug," active pharmaceutical agent," "pharmacologically active agent" are interchangeable and include, without limitation, prescription and non-prescription pharmaceutical compounds, as well as pharmacologically effective doses of vitamins, cofactors, and the like. Not considered a "drug" herein are such substances as foodstuffs or vitamins in "recommended daily allowance" quantities.

The term "interface" refers to that part of the tablet representing the region at which two layers adjoin one another.

The term "undetectable amount" means that using conventional analytical techniques such as high performance liquid chromatography (HPLC), nuclear magnetic resonance (NMR) and the like, the presence of an active compound can net be detected. The term "pharmacologically ineffective amount" means an amount that has no pharmacological effect. It is understood that due to the conditions under which high speed automated tabletting equipment are operated, some unintentional mixing of different granulations may occur which may cause amounts, preferably trace, of one granulation to appear in a segment where it was not intended to be placed.

The terms "horizontal," "transverse," and "vertical" when used in relation to a tablet, are based on the spatial orientation of the tablet as, and after, it is produced in a die, but before removal or ejection from the die. The first granulation into a tablet die produces the bottom layer. In the tablets of the invention, most often said first layer becomes a divided layer after tamping or final compression, a divided layer from which a plurality of unitary segments are created. Said first granulation, divided layer, and unitary segments occupy the bottom of said tablet. If said tablet is composed of said unitary segments and a second, undivided layer that forms another segment that is not a unitary segment, then said non-unitary segment represents the top of said tablet. The parts of the tablet that are in contact with the internal, usually vertically-oriented faces of said tablet die are the sides of said tablet.

A tablet of the invention containing a bottom divided layer and a top undivided layer, and no other layers, is usually wider than it is tall. The width is the greatest transverse dimension representing the perimeter of the transverse cross-section tablet, such as the longer side of a rectangular (non-square) perimeter. When the invention is created with a bottom embossing that separates the bottom layer to become a divided layer, preferably said embossing also penetrates into the immediately superior segment to cause said superior segment to have a score.

The following describes a method of manufacture of a preferred embodiment of the invention:

A granulation enters the die of a tablet press, such as a standard bilayer high-speed press. The granulation is optionally tamped and forms a layer that is indented from below by an embossing present on the bottom punch. Said embossing may be in the form of a bisecting embossing or may be more complex and may involve more than one score. At a second filling station, a second, non-identical granulation that is preferably comprised of inactive excipients enters the die and is optionally tamped. At the same filling station, a full compressive force is applied, sufficient to push both layers downward, so that the first, bottom layer is pushed substantially completely to the level of the upper part of the embossing of the bottom punch. If said uppermost aspect of said embossing reaches up to or, preferably, into said second layer, then a novel tablet has been created. This tablet comprises as its first layer what is called herein a divided layer. The discrete parts of a divided layer are without contiguity and are called unitary segments herein.

A layer is thus formed when a granulation has completely entered a tablet die. A layer is considered to be present after said granulation has fully entered said die, after any tamping has occurred, and after final compression to form a compressed tablet. Tablets of the current invention require two compositionally non-identical ("different") granulations and therefore are formed from a plurality of layers.

Functional units of the compressed tablets of the invention are generally referred to as segments, not layers, because of the following considerations. If two identical granulations were poured sequentially into the die at two consecutive filling stations, then the compressed tablet containing both layers formed from said granulations would not be in practical terms distinguishable from each other; they would function as one segment (a "compound segment" herein, as such a segment is formed from a plurality of contiguous layers). A segment formed from one layer is a simple segment. The novel segments of the invention generally derive from one layer. The divided layer gives rise to two or more "unitary segments." In the less preferred case that two consecutive substantially identical granulations enter the die consecutively and both become divided and then a compressed tablet is formed, then unitary segments that are also compound segments will have been formed.

In addition, the invention requires a layer to be divided. Each non-contiguous part of the tablet formed from the parts of a layer may be considered a segment. In general, tablets of the invention are formed from one divided layer that gives rise to two or more segments. Segments formed from a divided layer are called "unitary segments" herein. In certain cases, however, two compositionally substantially identical granulations may enter the die and both give rise to divided layers. The contiguous parts of the divided layers would then comprise unitary segments that have the feature described above of being "compound."

In most cases, the basic invention will tend to have one "supporting" or "backing" layer that is also denoted as a segment. A segment formed from one layer not contiguous with a compositionally substantially identical layer is a simple segment. In most cases, a unitary segment is formed from one layer and is therefore also a simple segment.

Current methods of manufacture produce tablets with one granulation entering the die on top of another, so that tablets of the invention produced in such a manner comprise one or more top (outer) segments, one or more bottom (outer) segments, and optionally one or more inner segments. A segment that is not a top or bottom (i.e., outer) segment is considered to be an inner segment. Inner segments have sides that are external and that may play an important role, as they may come to be scored, broken through, etc., if the tablet contains unitary segments adjoining a first segment not formed from a divided layer, and said first segment on its face opposite that adjoining said unitary segment adjoins another segment. Neither the number of inner segments, nor the number of unitary segments that adjoin an inner segment, is limited to one.

Certain important embodiments of the invention involve one or more additional segments added vertically on top of the segment that adjoins a bottom divided layer (i.e., a plurality of unitary segments). In one case, a compositionally substantially identical granulation to that forming said bottom divided layer may comprise the upper segment of the tablet. Thus, the tablet may comprise three layers and four segments: two bottom unitary segments formed from one layer; an inner segment formed from an inactive granulation that has adequate height to be broken substantially through said segment only; and, a top segment containing substantially the same granulation in the same quantity that formed the bottom divided layer. Thus, a tablet would thereby allow breaking through the inner segment into two parts ("tablettes") each of which contain the same quantity of drug (i.e., half the dose present in the whole tablet). Then, the tablet containing the unitary segments could further be divided to give two quarter doses.

In another preferred embodiment that is a variation of that described immediately above, an upper segment may comprise a different drug than does a bottom unitary segment. With regard to the unitary segments, the advantage over current practice remains.

Tablets of the invention are not limited in dimensions or number of segments. Two or more unitary segments may be formed from a divided layer. A practical limit to the number of unitary segments formed from one layer in a tablet suitable as a whole tablet for human oral ingestion is eight. In addition, while less preferred, a tablet may have two different types of unitary segments, caused by the formation of two divided layers each formed from different granulations.

In addition, an undivided segment that adjoins unitary segments may be formed from a granulation that contains a different drug than that present in the granulation forming the unitary segments, or may contain the same drug as in said granulation but in a different, and most preferably diminished, concentration.

While not depicted in a diagram, a tablet may be formed from an inner undivided layer which has unitary segments on opposite faces.

In addition, it is technically feasible to produce unitary segments from a layer that leaves the die as an undivided layer, such as by taking a file or abrasive or cutting instrument and removing sufficient material from one segment to cause it to become a plurality of non-contiguous segments. Such a technique could allow an upper segment of the tablet described in the paragraph immediately above to be created. In addition, such a technique could also allow a two-layer tablet to exist in which each layer gives rise to a unitary segment. This could be done, for example, by taking the tablet of FIG. 1 and creating a notch, in a location other than directly over the score in the lower aspect of said upper segment, in a manner such as via a file, which extends into one of the unitary segments. Such an embodiment is a less preferred embodiment.

Figure 3:
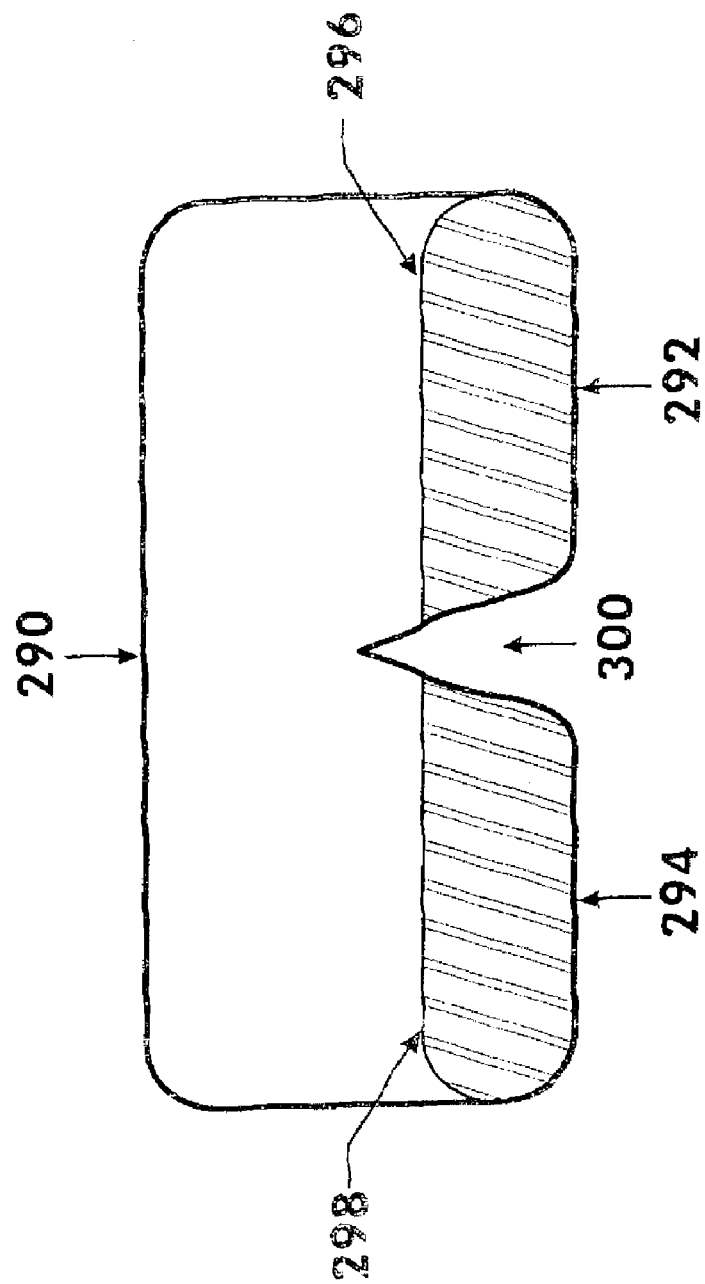
FIG. 3 depicts a cross-section of a three-segment tablet where the score is made with a triangularly shaped profile.
Figure 4A:
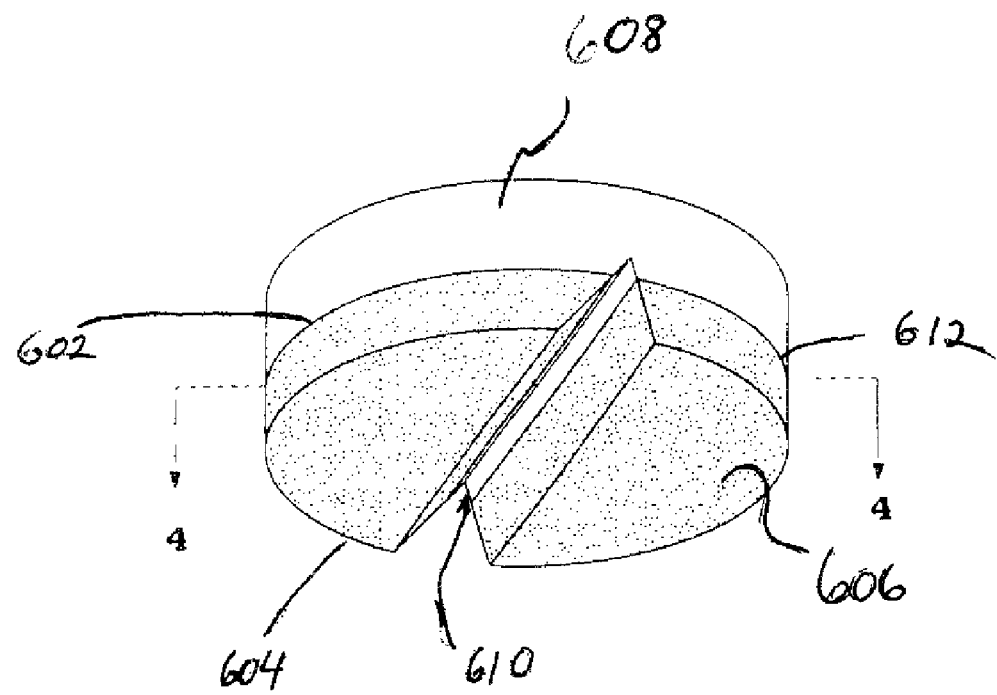
FIG. 4a depicts a bottom perspective view of a three segment tablet.
Figure 4B:
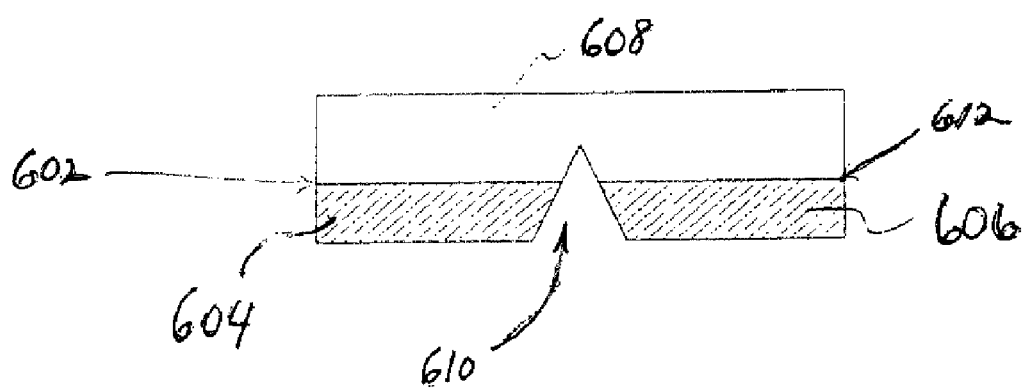
FIG. 4b is a cross-section of FIG. 4 taken along lines 4-4.

The novel dosage forms may contain a divided layer (or layers) and a plurality of unitary segments arising from said divided layer (or layers). Tablets of the invention with the structure as depicted in FIG. 1, FIG. 3, and FIG. 4 are intended to be broken, if it is desired to create accurate smaller doses of active drug than are present in the whole tablet, through the undivided, upper segment, such as by locating the space between two or more unitary segments and applying force to the undivided segment so that substantially all tablet breaking takes place in said undivided segment, that preferably contains a minimal amount of drug, or in some cases, contains a drug for which accurate breaking is of diminished importance. Examples of such drugs could include folic acid or "B complex" vitamins in pharmacologically effective doses, or potentially a drug that treats hypertension that has a wide dosage range over which the pharmacologic effect changes little. Alternatively, a tablet as in FIGS. 1, 3, and 4a-b, may be broken by grasping the tablet at its ends and applying force so that, as the potentially weakest region, breaking occurs centrally through the region of the non-unitary segments by the space between said unitary segments and gives the intended break.

The tablets of the invention may be broken in standard ways, according to the invention such as either by applying force such as a cutting edge directly to the desired breaking region as described above or by gripping the ends of the tablet and applying force so that the tablet breaks substantially completely through the undivided segment.

FIGS. 1-7 depict cross-sectional views of tablets and tablettes of the invention, except for FIG. 4a, which is an external view. The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet.

The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet.

"Front views" refer to a cross-sectional view of a tablet that has a theoretical geometric plane passed through the tablet relative to a side which is arbitrarily designated as the front. Figures labeled as "side view," which also have a corresponding "front view" are taken as a cross-section through the whole tablet from the right side of a front view i.e., a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view.

That plane is located half-way between the front and back surfaces of said tablet.

Cross-sections of segments are shown crosshatched if they contain a drug and if they lack a pharmacologically effective quantity of drug, they are shown plain (clear, without crosshatching or stippling). The upper part of each figure corresponds to the upper part of a tablet, all of which are depicted as they are situated within a die after final compression and before ejection from the die. For consistency, tablettes are depicted in the same orientation as the tablets from which they are formed, although tablettes are created after tablet ejection from a die.

Tablettes are depicted with broken surfaces as indicated by a fine saw-tooth pattern. Such saw-tooth depiction is schematic and not intended to represent the actual pattern of breaking of a tablet or tablette.

Tablets of the invention have the core structure A'A"/X where A'A" represents the substantially identical unitary segments formed from a (completely) divided layer most preferably containing a drug; X represents a segment generally representing an undivided layer and one face (surface) of X adjoins both A' and A"; X is preferably scored on the surface to which A' and A" adjoin, to aid tablet breaking. (X may optionally be scored on another surface, as well.) The number of unitary segments formed from a layer is not limited to two; a bottom embossing pattern involving three parallel scores or two crossing scores may allow four compositionally substantially identical unitary segments to be produced.

Tablets of the invention may be manufactured by the above technique and related techniques. For example, a minimal amount of granulation may enter the die and rest on an embossed lower punch. If the embossing is high enough and the quantity of granulation is small enough, the layer formed from the granulation may be a divided layer even before any further compression occurs; this situation is less preferred, however, as there may not be the generally desired equality of mass between said unitary segments. In another example, a first and second feed of substantially identical granulations may enter the die onto an embossed lower punch with one bisecting score, followed by a third, non-identical feed. If final compression pushes said first and said second granulation below the uppermost part of said embossing, then the first two granulations will have formed two divided layers of a three-layer tablet, but collectively the two divided layers will have formed two and not four unitary segments; each segment will consist of approximately half of each divided layer.

In another example, a layer may not comprise a divided layer until a tablet has been formed and ejected from the die. In such a case, application of force, such as by a knife or a cutting instrument, may be utilized to remove sufficient material containing drug so that a score is cut into the undivided segment. This technique could be useful in cases in which an upper punch contains an embossing and a deep score is created in the upper segment, but a small amount of said segment remains, and could be removed subsequent to tablet ejection from the die.

FIG. 1 depicts a tablet containing unitary segments 272 and 274 in vertical cross-section, front view. Both of said unitary segments adjoin the same face (surface) of segment 270, which is formed from a single granulation and due to mixing of granulations, contains a minimal amount of the drug that is present in segments 272 and 274. Interfaces 276 and 278 represent the regions at which segment 270 adjoins segments 272 and 274, respectively. Score 280 indents segment 270 and also represents the space between segments 272 and 274.

Figures 2A, 2B:
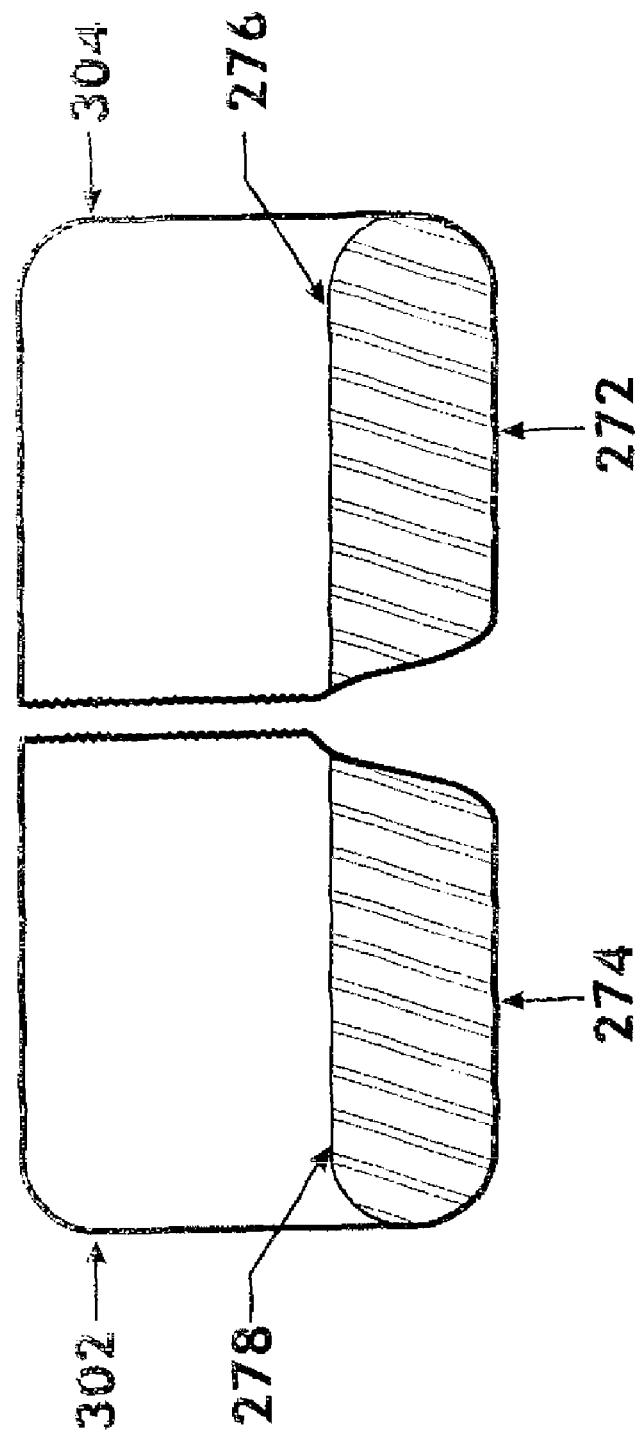
FIGS. 2a-b depict cross-sections of the tablettes made by breaking the tablet of FIG. 1.

FIGS. 2a and 2b depict the two tablettes created by breaking the tablet of FIG. 1 through segment 270. In FIG. 2a, segment 302 represents that part of segment 270 that adjoins intact segment 274. Interface 278 represents the region at which segments 302 and 274 meet. In FIG. 2b, interface 276 represents the region at which segments 304 and 272 meet. Score 280 and segment 270 of FIG. 1 are not considered to exist once the tablettes are formed. Each tablette of FIGS. 2a and 2b contains substantially equivalent mass assuming the score 280 of FIG. 1 is a bisecting score relative to the layer that became divided in the creation of segments 272 and 274.

Tablets of the nature of that of FIG. 1 may contain in the unitary segments a mixture of drugs or, as in FIG. 1, one drug. In addition, the granulation that forms segment 270 of FIG. 1 may be provided with a drug that is the same as, or different than, that of the divided layer. In this case, it would be likely that said drug provided in the upper layer would have a therapeutic effect and side effect profile that was not very sensitive to accuracy of subdivision of a dose.

In addition, no limitation exists as to the presence of one or more additional segments created superior to (i.e., above) 270, or the composition of such. Also, though less likely, there could be another set of different unitary segments inferior to (i.e., below) segments 272 and 274.

FIG. 3 depicts a tablet similar to that depicted in FIG. 1, but the tablet of FIG. 3 has a score 300 that extends more deeply into the non-unitary segment 290 than does score 280 of FIG. 1. One way of producing score 300 is to use the embossing and manufacturing technique used for the tablet of FIG. 1 and then remove, such as with a file, material from segment 290. Alternatively, embossing of the appropriate size and shape may be able to be utilized to create score 300 directly. The tablet of FIG. 3 contains unitary segments 292 and 294. Interfaces 296 and 298 are present between segments 292 and 290, and 294 and 290, respectively.

FIG. 4a depicts an external view of a tablet containing unitary segments 604 and 606 that are at the bottom of the tablet. In this tablet, score 610 penetrates into clear, upper, non-unitary segment 608. Interface 602 represents the region at which segment 608 meets segment 604. Interface 612 represents the region at which segment 606 meets segment 608.

FIG. 4b depicts the same tablet depicted in FIG. 4a. This vertical cross-section is taken perpendicularly through score 610, which occupies the diameter of the circular transverse cross-section of the tablet.

Figure 5:
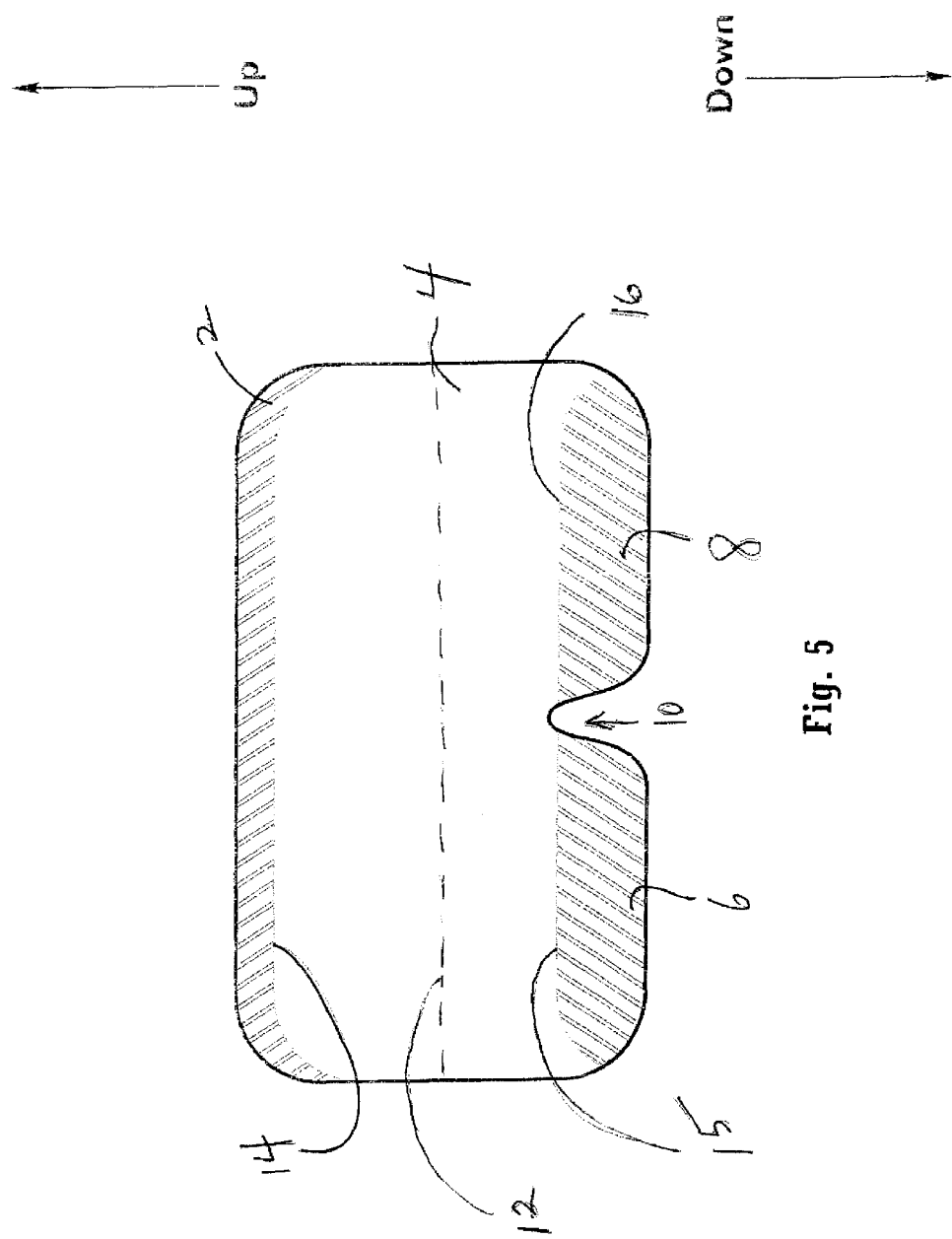
FIG. 5 is a cross-section of a four segment tablet with a score.

FIG. 5 depicts a tablet containing four segments. Unitary segments 6 and 8, as with all unitary segments, are not contiguous with each other. Score 10 penetrates into segment 4. Segment 4 is a compound segment formed from substantially compositionally identical inactive granulations added sequentially. Top segment 2 contains a therapeutic quantity of a drug that differs from the drug that is present in a therapeutic quantity in segments 6 and 8. Dotted line 12 reflects a surface score that runs transversely across segment 4. A preferred horizontal dimension for the tablet of FIG. 5 is 12-18 mm, but said dimension is not limited. Interface 14 depicts where segments 2 and 4 are contiguous. Interfaces 15 and 16 depict where segments 6 and 8, respectively, adjoin segment 4. Segment 4 contains therapeutically insignificant quantities of the drugs found in segments 6 and 2.

The tablet of FIG. 5 may be broken usefully in two ways. One way is vertically through score 10 in the direction of segment 2; such breaking would not utilize the score reflected by dotted line 12, but would give a dose of half of the drug found in segments 6 and 8, though likely would not give a precise halving of the drug found in segment 2, due to difficulties with breaking scored tablets as was documented in the Background of the Invention, above. The result of another way of breaking said tablet is depicted in FIGS. 6a and 6b.

Figure 6A:
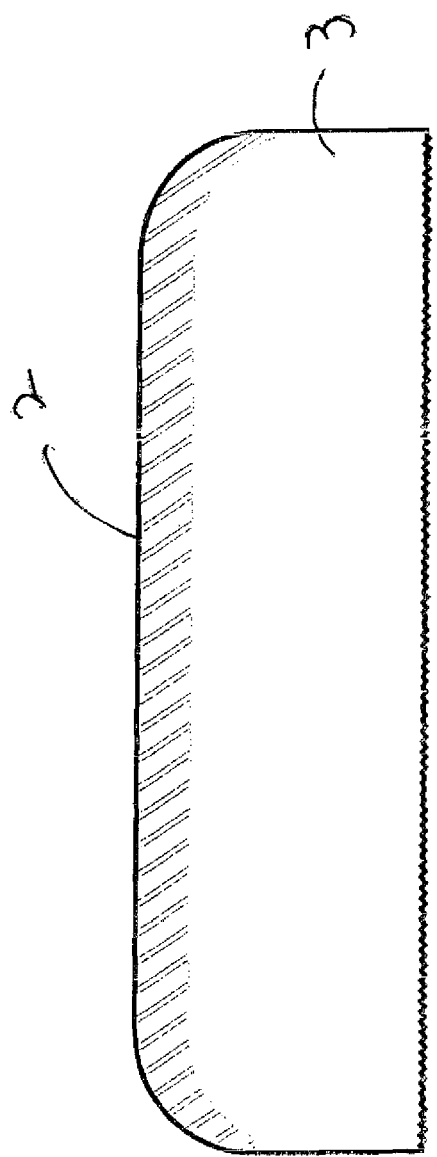
FIGS. 6a-b depict two tablettes made by breaking the tablet of FIG. 5.

FIG. 6a shows a tablette formed from breaking the tablet of FIG. 5 through the horizontal score reflected by dotted line 12. As with other tablettes depicted herein, it is not assumed that breaking is even, but the tablettes are depicted so that breaking is contained substantially within segment 12, that is a segment interposed between upper segment 2 and lower segments 6 and 8 in the tablet of FIG. 5. The tablette of FIG. 6a demonstrates that segment 2 is intact, as is interface 14.

Segment 3 is formed by the part of therapeutically inactive segment 4 of the tablet of FIG. 5 that remains contiguous with segment 2. The tablette of FIG. 6b depicts segments 6 and 8, and interfaces 15 and 16, as unchanged from the tablet of FIG. 5. Segment 7 is the part of segment 4 of FIG. 5 that becomes part of the tablette of FIG. 6b.

Figure 6B:
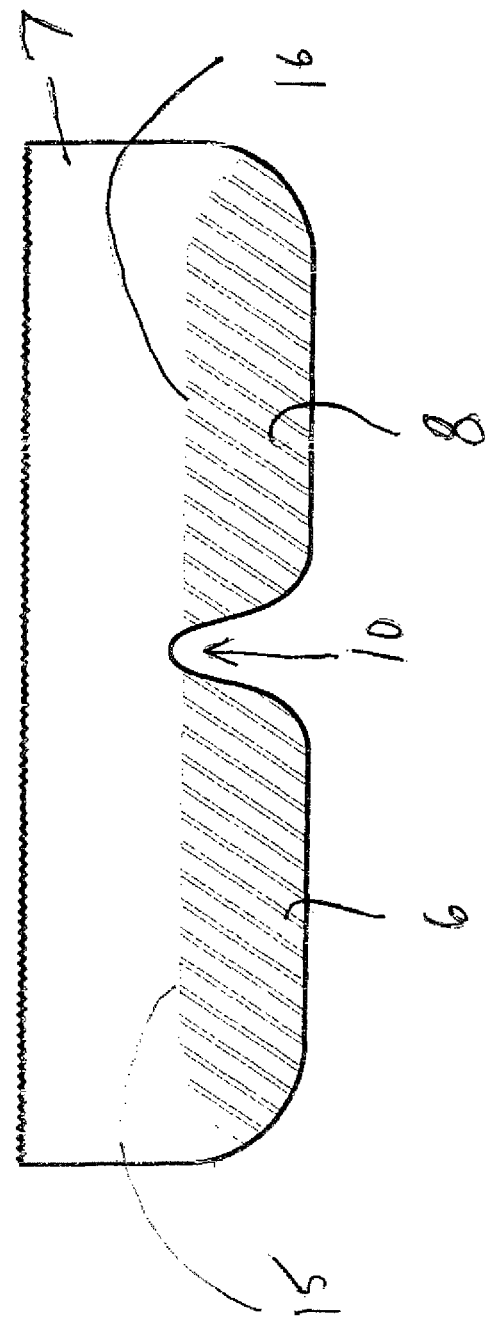
Figure 7A:
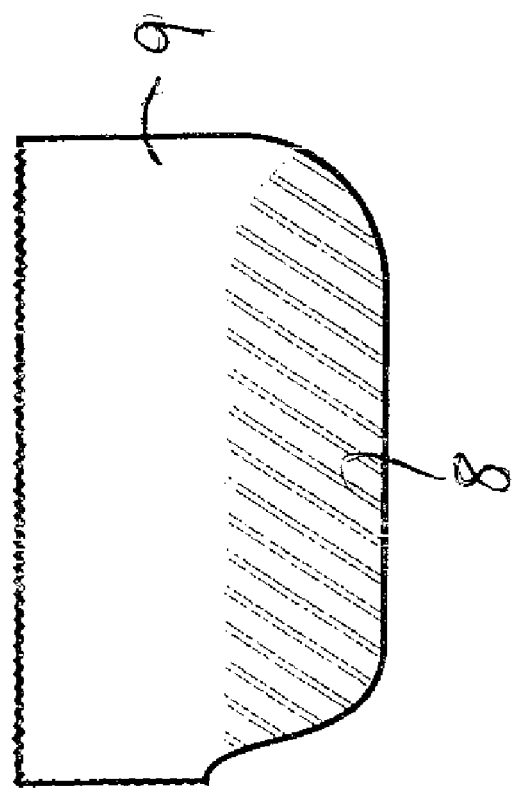
FIGS. 7a-b depict two tablettes made by breaking one of the tablettes of FIG. 6b.
Figure 7B:
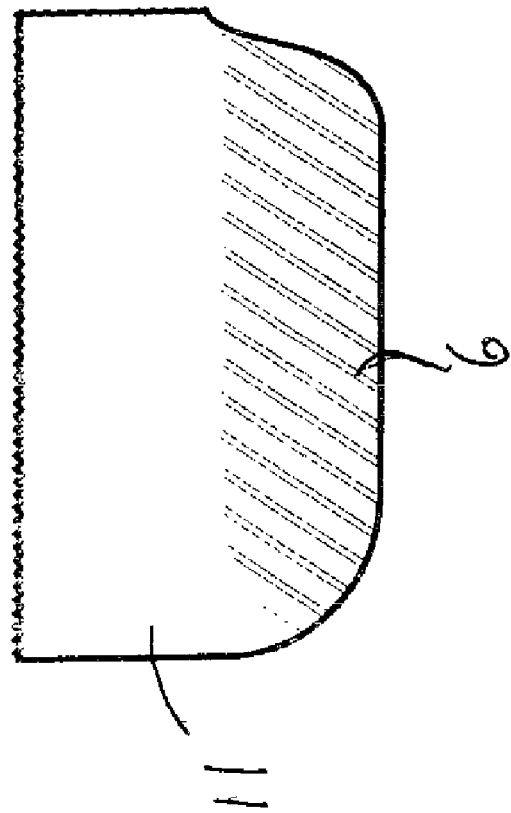

FIGS. 7a and 7b depicts the result of a second breaking, that of the tablette of FIG. 6b. FIG. 7a depicts segment 8 that now adjoins new segment 11, formed from segment 7 of the tablette of FIG. 6b. Interface 16 and segment 8 are unchanged from that of the whole tablet of FIG. 5. FIG. 7b depicts segment 9, formed from segment 7 of FIG. 6b, and segment 6 and interface 15, which are unchanged from the whole tablet of FIG. 5.

Thus, FIGS. 7a and 7b, in association with FIGS. 5, 6a, and 6b, demonstrate a means by which a combination tablet can be divided not only to separate therapeutic quantities of one active drug from another, but also then precisely give a partial dose of one of said active drugs.

The invention also includes the method of administering one or more drugs via the dosage forms such as tablets and tablettes of the invention to a patient, mammal, or other animal in need of pharmaceuticals for the prevention or treatment of an illness, maintenance of good health, retarding of aging, or other purpose. Included are methods of treating a patient with only one drug from a combination product, such as with a novel tablette of the invention, enabling downward dose adjustment for a variety of reasons; or, in a similar vein, a patient may be treated with one whale tablet containing a plurality of active drugs and in addition receive only one drug from a similar tablet, thus enabling upward dose adjustment. Combination products that can benefit from the invention, in which one drug is in an outer active segment, and a second and different drug is in the other outer active segment, and an inactive middle segment as in embodiments such as was described in paragraphs 3 and 4 above, include those containing the following pairs of drugs: amlodipine and either benazepril, chlorthalidone, or atorvastatin; benazepril and hydrochlorothiazide; olmesartan and hydrochlorothiazide; and many others, including the majority of the currently-produced combination products. Also included is the method of treating a patient with a precise partial dose of medication from a whole tablet, which may be a half or quarter of the whole dose, but may usefully be a different fraction. Warfarin especially may usefully be produced and dosed according to the invention with separable segments of the tablet that may but need not be as halves, quarters, etc. L-thyroxine and digoxin are other examples that could so benefit, along with warfarin.

The following give possible clinical situations in which the tablets of the invention could provide important benefits.

1. A currently marketed product in the United States is Caduet®, which contains the active ingredients atorvastatin calcium (atorvastatin) and amlodipine besylate (amlodipine) which are largely homogeneously inter-dispersed in an unscored tablet. The product is indicated to treat both hyperlipidemia (atorvastatin) and hypertension (amlodipine). A patient ingesting this tablet daily may then undergo a blood test and be diagnosed as having liver dysfunction as manifested by elevation of an enzyme's concentration in the blood. The physician may then recommend cessation, possibly temporary, of atorvastatin, which is stated by the manufacturer to be a possible cause of liver dysfunction. A patient receiving Caduet, however, would have to thus also discontinue amlodipine, which is not in this example desired by the physician. A tablet of the invention in which atorvastatin and amlodipine were segregated in different outer active segments, separated by a middle segment of adequate dimensions, would be a clear advance over the current Caduet formulation, because such a tablet would allow a patient to promptly continue ingesting amlodipine while stopping ingestion of atorvastatin, without having to go to a pharmacy and fill a new prescription for a tablet containing only amlodipine as the active ingredient, while having previously had the convenience of having both drugs combined in a single dosage form. The above embodiment of the invention represents an improvement over the current Caduet dosage form.

Another clinical situation in which the invention is superior to Caduet is one in which a patient receiving amlodipine 5 mg once daily and atorvastatin 20 mg once daily is advised by a physician to increase the daily amlodipine dose to 10 mg once daily. A patient in possession of adequate tablets of the invention, with the active drugs segregated in a three-segment tablet, would be able to promptly increase the amlodipine dose by taking a whole tablet of the invention once daily, plus a tablette containing 5 mg of amlodipine, produced by breaking a second whole tablet of the invention.

Another clinical situation in which the invention is superior to Caduet involves the case in which a physician wishes a patient to ingest atorvastatin 20 mg each morning and amlodipine 2.5 mg twice daily. The invention provides for amlodipine to be separated from atorvastatin and then broken precisely in half. The invention thus allows the patient the advantage of one tablet, whereas to accomplish this currently in the United States would require one 20 mg Lipitor® (atorvastatin) tablet and two Norvasc® (amlodipine) 2.5 mg tablets.

2. The combination of amlodipine besylate and benazepril hydrochloride (benazepril) is marketed in the United States under the brand name of Lotrel®. This product is a capsule that is routinely ingested whole. An embodiment of the invention provides a whole tablet containing one outer segment containing amlodipine as the only active drug and the other outer segment containing benazepril as the only active drug. If desired, either outer layer may be formed into more than one segment, as in FIG. 1a. As in example 1 above regarding Caduet, the middle segment is inactive and may be broken through to create two tablettes, each comprising a whole amount of each outer active segment plus approximately half of the amount of the middle inactive segment. If a patient were to develop a need for double the dose of one active drug but not the other, the tablet of the invention could meet that need. Alternatively, if a patient were to develop a need to ingest only one active drug, possibly temporarily, due to such conditions as blood pressure changes or a side effect to one drug but not the other, the tablet of the invention allows this to be done without a new dosage form being prescribed.

3. Another use of the invention involves the combination of amlodipine and chlorthalidone or another diuretic, which may usefully be combined to treat hypertension. Benefits of the invention are similar to those described in the paragraph immediately preceding this paragraph.

4. Another use of the invention involves the combination of olmesartan medoxomil (olmesartan, an angiotensin receptor blocker) and hydrochlorothiazide (HCTZ). This product is currently marketed in the United States under the name Benicar/HCT®, with the doses, respectively, of, in mg: 20/12.5, 40/12.5, and 40/25. A very common starting dose of a patient will be 20/12.5 once daily. The product is currently marketed in all strengths as a homogeneous tablet containing both active drugs. Formulated according to the current invention, a patient who begins treatment with the 20/12.5 dose may be increased with the same tablet to each of the other doses by ingesting one whole 20/12.5 tablet and either a half tablet containing 20 mg of olmesartan or a half tablet containing 25 mg of HCTZ. This will provide the physician an opportunity to investigate the new dose before giving the patient a new prescription. Other advantages of the invention are similar to those described above.

5. Another useful combination product that may be formulated according to the invention involves angiotensin converting enzyme inhibitors (ACEs) and diuretics such as HCTZ. Both types, of drug not uncommonly have side effects, so that the invention will be useful to physicians in dealing with the side effects, as well as with changing dosing needs to deal with the anti-hypertensive and other clinical benefits of the drugs.

6. Another product that may benefit from the invention regarding separating active drugs in separate outer layers with an inactive middle segment (layer) is a combination product containing two active drugs, fluoxetine and olanzapine.

No limitation to the above therapeutic fields or to the specific examples within their fields is intended for tablets of the invention, which may be used in any suitable combination of drugs. No limitation to two-drug combinations exists, as well. For instance, one outer active segment of a tablet according to the invention could contain levodopa and carbidopa, and the other outer active segment could contain entacapone, a tablet product containing all three drugs in a homogeneous fashion that is currently marketed in the United States as Stalevo®. Also, a tablet per the invention could involve five layered segments, with, for example, amlodipine in one outer segment, an inactive segment adjoining it, a middle segment containing chlorthalidone or HCTZ, and a second inactive Segment adjoining both it and the other outer segment that contains benazepril (see FIG. 8). If both inactive segments were of adequate dimensions to be conveniently breakable without damaging any of the three active segments, thus providing significant clinical advantages due to the adoption of flexible dosing of the different active segments.

The following list of possible combinations of a plurality of drugs is exemplary and not limiting. The combinations referred to may include two or more members of the classes listed. Drugs listed below, and herein, may for convenience exclude mention of any salt of a drug; e.g., "atorvastatin" is listed even though its marketed form is atorvastatin calcium.

Without limitation, useful combinations may include a plurality of drugs from within the following six drug classes. In addition, tablets of the invention may be created containing only one of a drug from the following list. With regards to combination use, two methods of use may apply to the invention. One of these methods is to place an individual drug in a granulation and a different individual drug (or combination of drugs) in a different granulation, potentially with an inactive granulation interposed between them; another method is to place a plurality of drugs in one or more segments.

1. Anti-anginal agents, for example:
   A. Calcium antagonists (see list below);
   B. Beta-blocker (see list below);
   C. Organic nitrate preparation (e.g., isosorbide mononitrate or dinitrate).
2. Anti-anginal agent plus an anti-platelet agent, such as aspirin, clopidogrel, or ticlopidine.
3. Two hypoglycemic agents (see list below).
4. Potassium chloride and any thiazide-type or loop diuretic (see lists below).
5. Lipid-lowering agent plus: hypoglycemic agent, anti-platelet agent, anti-anginal agent, and/or antihypertensive agent (see lists above and below)

Hypoglycemic agents include: thiazolidinediones: pioglitazone, rosiglitazone; sulfonylureas: glyburide, glipizide, glimepiride, chlorpropamide;
   Biguanides: metformin;
   Meglitinides: nateglinide, repaglinide;
   Glucosidase inhibitors: acarbose, miglitol.
6. Antihypertensive agents:
   Beta-blockers: acebutolol, atenolol, bisoprolol, celiprolol, metoprolol, mebivolol, carvedilol (a mixed alpha-beta blocker), nadolol, oxprenolol, penbutolol, pindolol, propranolol, timolol, betaxolol, carteolol;
   Calcium antagonists (calcium-channel blockers): nifedipine, amlodipine, verapamil, diltiazem, nisoldipine, felodipine, isradipine, lacidipine, lercanidipine, nicardipine, manidipine;
   Thiazide-type diuretics (with or without potassium-retaining diuretics such as triamterene, amiloride, or spironolactone): hydrochlorothiazide, chlorothiazide, cyclopenthiazide, polythiazide, bendrofluazide, hydroflumethiazide, chlorthalidone, indapamide, methylclothiazide, metolazone;
   Angiotensin converting enzyme inhibitors: captopril, enalapril, lisinopril, ramipril, trandolapril, quinapril, perindopril, moexipril, benazepril, fosinopril;
   Angiotensin receptor blockers: losartan, valsartan, candesartan, telmisartan, eprosartan, irbesartan;
   High-ceiling (loop) diuretics (with or without potassium-retaining diuretics such as triamterene, amiloride, or spironolactone): furosemide, torsemide, ethacrynic acid, bumetamide;
   Aldosterone antagonist diuretics: spironolactone, eplerenone;
   Alpha-blockers: doxazocin, terazosin, prazosin, indoramin, labetolol (a mixed alpha-beta blocker);
   Central alpha-agonists: clonidine, methyldopa;
   Imidazoline: moxonidine;
   Direct vasodilators: hydralazine, minoxidil;
   Adrenergic neuronal blocker: guanethidine.
   Lipid-lowering agents include:
   Statins: lovastatin, simvastatin, pravastatin, rosuvastatin, atorvastatin, fluvastatin;
   Fibrates: clofibrate, bezafibrate, fenofibrate, gemfibrozil, ciprofibrate;
   Others: ezetimide, niacin, acipimox.

The combinations of drugs disclosed herein are for illustrative purposes and are not intended to limit the scope of the invention.

Regarding the important usage of the tablets and tablettes of the invention, that involving division of a tablet into tablettes containing similar active segments, most drugs that may undergo dosage adjustment will be preferred if they may be divided in an optimally precise manner. Examples of drugs that will especially benefit from the advances of the invention in this manner include narrow therapeutic index drugs such as warfarin, digoxin, L-thyroxine; vasoactive drugs such as amlodipine; hypoglycemic agents such as rosiglitazone and glipizide; and anxiolytics drugs such as alprazolam. These are however but a small fraction of the great mass of drugs that will benefit from the various embodiments and procedures of the invention.

There are numerous methods of use of the dosage forms of the invention, including its tablets and tablettes. Persons skilled in the medical and pharmaceutical arts will recognize the many advantages that the various embodiments of the invention allow over current products. Some examples of benefits of the inventions involving tablets containing exactly one similar active segment are described immediately below.

1. Warfarin is an anticoagulant marketed in the U.S. under the brand name Coumadin®, which is a scored tablet. Research has shown that patients do not break warfarin 5 mg tablets into equal 2.5 mg segments. The invention teaches different types of tablets that allow warfarin tablets of any common human dose to be broken into precise halves, and potentially precise thirds, quarters, etc. (tablettes). Thus a patient may utilize warfarin half-tablets (tablettes) produced as per the invention with similar confidence as in the whole tablet. Because warfarin doses are frequently broken, many clinical scenarios exist in which the invention will benefit patients.

2. Norvasc (amlodipine besylate or amlodipine herein) is marketed as unscored 2.5, 5, and 10 mg tablets in the U.S. These tablets are of irregular shape and are difficult to break. The FDA-approved dosage range is from 2.5 to 10 mg ingested orally daily. The invention allows improved functionality of amlodipine. For example, under the invention, a patient receiving 5 mg daily who a physician wishes to increase to 7.5 mg daily may simply utilize a tablet of the invention that comprises two separate 2.5 mg segments to increase the dose to precisely 7.5 mg, such as by ingesting one whole 5 mg tablet and one 2.5 mg tablette created by breaking a 5 mg tablet into two tablettes each containing 2.5 mg of amlodipine. Convenience and cost savings are clear. Similarly, a patient receiving a 10 mg dose of Norvasc who is advised to reduce the dose to 5 mg daily must currently purchase a new prescription for 5 mg Norvasc tablets. The invention provides the ability to provide a 10 mg tablet that may be broken into two tablettes, each containing precisely 5 mg of amlodipine. The invention may therefore enable greater flexibility of treating patients, and provide cost savings as well. A further benefit of the invention is that various embodiments allow fully accurate separation of a tablet into a tablette comprising one-fourth of the dose of the active ingredient as is found in the whole tablet. This may for example be done for amlodipine by providing four active segments all containing 2.5 mg of amlodipine.

Thus, a 10 mg amlodipine tablet of the invention may be utilized to provide a 7.5 mg dose; or, it may be utilized to provide four 2.5 mg doses.

A further benefit of the invention may relate to pediatric or geriatric doses, which may not be produced in appropriate dose strengths. In the case of amlodipine, a 1.25 mg daily dose may be useful in either small children with hypertension, or in frail elderly patients with angina or hypertension, who may have hepatic dysfunction. Even though the United States Food and Drug Administration (FDA) has not approved a 1.25 mg dose, precise divisibility of the approved 2.5 mg dose would allow a 1.25 mg daily dose. In addition, precise divisibility of the approved 2.5 mg dose will allow accurate dosing of 3.75 mg.

Another use of the invention is to enable a method of cost savings for insurers and patients. The invention allows this because many drugs, such as Norvasc and Coumadin, have pricing that differs little (if at all) between different doses. Because tablet splitting is imprecise for most scored tablets, the practice of mandatory splitting has been met with disapproval by most physician and pharmacist organizations. The invention enables tablet splitting because it provides accurate dosing when a tablet (or some tablettes, as in FIG. 1b) of the invention are broken as described herein. Substantial benefits are foreseen from this innovation. In addition, the ability to separate one active drug from another in a combination product has cost saving advantages, as well.

It is recognized that related inventions may be within the spirit of the disclosures herein. Also no omission in the current application is intended to limit the inventors to the current claims or disclosures. While certain preferred and alternative embodiments of the invention have been set forth for purposes of disclosing the invention, modifications to the disclosed embodiments may occur to those who are skilled in the art.

DESCRIPTION OF THE PREFERRED EMBODIMENTS

A tablet having two unitary segments containing equal amounts of amlodipine adjoining a first upper segment having no drug is made as follows:

A Stokes 27-station tri-layer rotary tablet press is used. All formulations are directly compressible powder blends. The blending of the amlodipine formulation is performed in a Patterson-Kelly "V" blender. The first segment consists of Nu-Tab® and requires no blending. The tablets are compressed using tablet punches to a hardness of 35 kilopounds. The amlodipine formulation is introduced first into a die having a wedge shaped embossed bottom section die sized to provide a total of 5 mg of amlodipine besylate in each dose. A top die having a flat profile is used to compress the tablet forming ingredients.

| Bottom Segment | Mg. |
| --- | --- |
| Dibasic calcium phosphate anhydrous | 51.13 |
| Amlodipine besylate | 7.15 |
| Sodium starch glycolate (Explotab ®) | 2.48 |
| Magnesium stearate | 0.93 |
| FD&C Blue #1 Aluminum Lake | 0.31 |
| Total | 62.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

| Top Segment | Mg. |
| --- | --- |
| Nu-Tab ® (Compressible sugar 30/35 N.F.) | 194.00 |

Manufacturing Instructions
1. Weigh each ingredient.
2. Screen each ingredient.
3. Triturate the color with the major diluent in geometric proportions using a suitable mixer.
4. Add the remaining ingredients, except the lubricant, to the color mixer from step #3 and mix for desired time.
5. Add the lubricant to the blend from Step #4 and mix for desired time.
6. Add the blend to a suitable press fitted with the desired tooling and compress into tablets.

Tabletting Instructions
1. Place the powder for amlodipine unitary segments (layer #1) in hopper #1.
2. Place the powder for first segment in hopper #2.
3. Place the powder for active layer in hopper #3.
4. Compress unitary segments to desired weight (tablets for layer #1 should form a soft compact)
5. Compress layer #1 & Layer #2 tablets to desired combined weight of layer #1 and layer #2 weight (tablets should form a soft compact)
6. Compress the bi-layer tablet to the desired total tablet weight (layer #1 weight+layer #2 weight Tablet should be at desired hardness.

The invention claimed is:

1. A compressed, layered pharmaceutical tablet formed in a tablet die having an embossed bottom tablet punch and a top tablet punch, said tablet comprising
one or more layers of a powder or granulation composition containing an effective amount of one or more active drugs, wherein said active drug-containing composition is filled into the tablet die wherein the embossed bottom tablet punch forms a divided active bottom layer or layers, said bottom layer or layers being tamped using the top tablet punch to provide first and second unitary segments each having a level top surface following said tamping; and
one or more layers of a second powder or granulation composition containing either an undetectable amount of drug or a pharmacologically ineffective amount of drug, wherein said second composition is filled onto the level top surface of said first and second unitary segments in the tablet die, said second composition forming an undivided, non-unitary inactive top segment having a bottom and top surface, wherein only the bottom surface contacts said level top surfaces of said first and second unitary active segments,
wherein the bottom active unitary segments and top inactive non-unitary segment are compressed to form a whole tablet, said tablet being divisible by breaking through the inactive non-unitary segment, without breaking of the first and second unitary segments,
wherein the terms "bottom" and "top" refer to the orientation of the tablet in the tablet die during compression.

2. A pharmaceutical tablet as defined in claim 1 in which one or more additional unitary segments in addition to said first and second unitary segments are optionally present and are derived from the same layer or layers as said first unitary segment.

3. A pharmaceutical tablet as defined in claim 1 in which the top inactive segment contains no more than 10 parts per million of the concentration of the drug or drugs present in said first unitary and said second unitary active segments.

4. A pharmaceutical tablet as defined in claim 1 in which the top inactive segment contains no more than 10% of the concentration of drug or drugs present in the first unitary segment and said second unitary segment.

5. A pharmaceutical tablet as defined in claim 1 in which the top inactive segment contains no more than 2% the concentration of drug present in the first unitary segment and said second unitary segment.

6. A pharmaceutical tablet as defined in claim 1 in which said top inactive segment is derived from a granulation that does not contain a drug.

7. A pharmaceutical tablet as defined in claim 1 in which additional unitary segments which are compositionally different from the composition of said first unitary segment and said second unitary segment and are derived from a granulation containing a drug.

8. A pharmaceutical tablet as defined in claim 1 in which said first unitary segment and said second unitary segment are outer segments.

9. A pharmaceutical tablet as defined in claim 1 in which said drug or drugs is or are pharmacologically effective in the treatment of cardiovascular conditions, psychiatric conditions, diabetes, thyroid disorders, pain or thrombotic disorders.

10. A pharmaceutical tablet as defined in claim 1 in which said drug is warfarin.

11. A pharmaceutical tablet as defined in claim 1 in which said drug is digoxin.

12. A pharmaceutical tablet as defined in claim 1 in which said drug is levothyroxine.

13. A pharmaceutical tablet as defined in claim 1 in which said first segment adjoins a plurality of unitary segments on the side of said first segment that is opposite the surface adjoining said first and second unitary segments.

14. A pharmaceutical tablet as defined in claim 1 in which a second segment which contains a drug adjoins said first segment on the side opposite the side where said first and said second unitary segments are located.

15. A method of breaking a pharmaceutical tablet as defined in claim 1 wherein said tablet is broken by applying force to said top inactive non-unitary segment to cause the tablet to break through said first segment.

16. A method of breaking a tablet as in claim 15 that comprises first breaking said tablet through said top inactive non-unitary segment to obtain a tablette that contains part of said first segment plus unitary segments and thereafter breaking said tablet between said first and said second unitary segments so that the tablet breaks substantially completely within said first segment.

17. A method of administering a partial dose of a drug contained in a pharmaceutical tablet, said method comprising breaking a pharmaceutical tablet according to claim 1 by breaking said tablet through said top inactive non-unitary segment to form two or more tablettes each containing a unitary segment and having a patient, other person, or other animal in need thereof ingest a tablette containing a unitary segment.

18. A method of administering a partial dose of a drug contained in a pharmaceutical tablet, said method comprising breaking a pharmaceutical tablet according to the method of claim 15 and having a patient, other person, or other animal in need thereof ingest a tablette formed by said breaking.

* * * * *